(12) United States Patent
Maruyama et al.

(10) Patent No.: US 10,898,878 B2
(45) Date of Patent: Jan. 26, 2021

(54) ADSORBENT MATERIAL

(71) Applicant: SHOWA DENKO MATERIALS CO., LTD., Tokyo (JP)

(72) Inventors: Masashi Maruyama, Tokyo (JP); Nanae Yamashita, Tokyo (JP); Yuzuru Shimazaki, Tokyo (JP); Hiroshi Yoshida, Tokyo (JP); Keisuke Shibuya, Tokyo (JP)

(73) Assignee: Showa Denko Materials Co., Ltd., Tokyo (JP)

( * ) Notice: Subject to any disclaimer, the term of this patent is extended or adjusted under 35 U.S.C. 154(b) by 0 days.

(21) Appl. No.: 16/301,303

(22) PCT Filed: Jul. 10, 2017

(86) PCT No.: PCT/JP2017/025139
§ 371 (c)(1),
(2) Date: Nov. 13, 2018

(87) PCT Pub. No.: WO2018/037742
PCT Pub. Date: Mar. 1, 2018

(65) Prior Publication Data
US 2019/0193050 A1  Jun. 27, 2019

(30) Foreign Application Priority Data

Aug. 23, 2016 (JP) .................. 2016-162834

(51) Int. Cl.
*B01J 20/26* (2006.01)
*B01D 15/38* (2006.01)
(Continued)

(52) U.S. Cl.
CPC .............. *B01J 20/26* (2013.01); *B01D 15/00* (2013.01); *B01D 15/02* (2013.01); *B01D 15/08* (2013.01);
(Continued)

(58) Field of Classification Search
CPC combination set(s) only.
See application file for complete search history.

(56) References Cited

U.S. PATENT DOCUMENTS

2005/0130191 A1* 6/2005 Fukushima ............ C07H 21/04
435/6.12
2010/0168395 A1 7/2010 Sato
(Continued)

FOREIGN PATENT DOCUMENTS

CN 102580685 A 7/2012
JP 6-319570 A 11/1994
(Continued)

OTHER PUBLICATIONS

International Search Report for PCT/JP2017/025139, dated Sep. 26, 2017.

*Primary Examiner* — Ellen M McAvoy
*Assistant Examiner* — Chantel L Graham
(74) *Attorney, Agent, or Firm* — Volpe Koenig

(57) ABSTRACT

An object of the present invention is to provide an adsorbent material having high dispersibility and reversibility. The adsorbent material has a polymer material having a plurality of functional groups ionizable in water and exhibiting no lower limit critical solution temperature, an adsorption site capable of interacting with a target substance, and a carrier.

10 Claims, 5 Drawing Sheets

(51) Int. Cl.
  *B01J 20/285* (2006.01)
  *B01D 15/02* (2006.01)
  *C12N 9/76* (2006.01)
  *C07K 16/00* (2006.01)
  *C07K 14/76* (2006.01)
  *C07K 1/22* (2006.01)
  *G01N 30/88* (2006.01)
  *B01J 20/28* (2006.01)
  *C12M 1/26* (2006.01)
  *B01D 15/00* (2006.01)
  *B01D 15/08* (2006.01)

(52) U.S. Cl.
  CPC ..... *B01D 15/3809* (2013.01); *B01D 15/3814* (2013.01); *B01D 15/3823* (2013.01); *B01J 20/28* (2013.01); *B01J 20/285* (2013.01); *C07K 1/22* (2013.01); *C07K 14/76* (2013.01); *C07K 16/00* (2013.01); *C12M 1/26* (2013.01); *C12N 9/6427* (2013.01); *G01N 30/88* (2013.01)

(56) References Cited

U.S. PATENT DOCUMENTS

2011/0017599 A1* 1/2011 Shimizu ............... C07K 7/06 204/548
2015/0191506 A1 7/2015 Okuyama et al.

FOREIGN PATENT DOCUMENTS

| JP | 7-136505 A | 5/1995 |
| JP | 2003-524680 A | 8/2003 |
| JP | 2005-176613 A | 7/2005 |
| JP | 2010-266334 A | 11/2010 |
| JP | 2014-219245 A | 11/2014 |
| JP | 2015-224332 A | 12/2015 |
| WO | 97/09068 A2 | 3/1997 |
| WO | 00/67901 A1 | 11/2000 |
| WO | 2008/143199 A1 | 11/2008 |
| WO | 2014/003176 A1 | 1/2014 |

* cited by examiner

ADSORBENT MATERIAL

TECHNICAL FIELD

The present invention relates to an adsorbent material and a purification method using the same.

BACKGROUND ART

Affinity purification of a biomolecule as a target substance like protein consists of steps of adsorption of the target substance on an affinity adsorbent material, washing away of non-adsorbing components, and desorption of the target substance from the adsorbent material by an eluent. At this time, the eluent to be used is a solution having a severe pH such as a strong acid or a strong base. This is because it is required that by changing the ionization states of an affinity ligand and the target substance, the interaction between the affinity ligand and the target substance is made weak by the charge repulsion. In a severe pH environment such as a strong acid or a strong base, however, biomolecules are often unstable and a risk of deterioration of a purified target substance arises. In order to avoid such a risk, a temperature-responsive affinity adsorbent material capable of purifying a target substance in a mild pH environment without pH change is developed.

As such temperature-responsive affinity adsorbent materials, reports are made on means using, as a ligand, a protein reduced in the thermal stability by gene recombination (Patent Literatures 1, 2) and means in which a polymer exhibiting a lower limit critical solution temperature (LCST), represented by poly(N-isopropylacrylamide) (PNIPAM), is used and phenomena such as phase transition caused by a change in the solubility to water accompanying a temperature change are exploited (Patent Literatures 3, 4).

However, it is difficult for the former means to serve as a practical adsorbent material because a gene recombinant protein is expensive and not high in durability.

Then, the latter means poses problems with the dispersibility and the reversibility of responsiveness due to that although problems with the price and the durability have been solved, since the affinity of a polymer for water largely decreases at temperatures of the LCST or higher, there are problems: the dispersibility of an adsorbent material in water extremely decreases, which makes handling of the adsorbent material difficult; in a column packed with the adsorbent material, flow paths through which a solution passes may largely change, and there arises a risk of generation of cracks and gaps between the adsorbent material and the wall surface; the hysteresis with respect to temperature change is often large; and the like, so the latter means hardly makes a practical adsorbent material (see FIG. 5).

CITATION LIST

Patent Literature

Patent Literature 1: International Publication No. WO2008/143199
Patent Literature 2: International Publication No. WO2014/003176
Patent Literature 3: JP Patent Publication (Kokai) No. 07-136505A (1995)
Patent Literature 4: JP Patent Publication (Kohyo) No. 2003-524680A

SUMMARY OF INVENTION

Technical Problem

As described above, conventional adsorbent materials using a polymer exhibiting an LCST, though being excellent in aspects of price and durability, which become problems in adsorbent materials using a gene recombinant protein, pose problems with the dispersibility and the reversibility of responsiveness. Hence, an object of the present invention is to provide an adsorbent material having high dispersibility and reversibility.

Solution to Problem

In order to solve the above problems, the adsorbent material according to the present invention comprises a polymer material having a plurality of functional groups ionizable in water and exhibiting no lower limit critical solution temperature, an adsorption site capable of interacting with a target substance, and a carrier; and the adsorbent material comprising these components leads to changes in the ionization rate of the polymer material in response to changes in the external environment. The adsorbent material according to the present invention does not use phenomena such as phase transition caused by a change in the solubility to water, and exploits, for adsorption and desorption of a target substance, changes in the ionization rate of the polymer material in response to changes in the external environment.

The present description includes the content of the disclosure of Japanese Patent Application No. 2016-162834 as the basis of priority for the present application.

Advantageous Effects of Invention

The adsorbent material according to the present invention, since not using a gene recombinant protein, can be produced inexpensively. The adsorbent material according to the present invention, since being low in the temperature dependency of the dispersibility in water, is easy in handling, and since not exploiting changes in the solubility of a polymer, is low in the hysteresis. The method for purifying a target substance according to the present invention can suppress the deterioration during purification of the target substance, and can also eliminate a neutralization step after purification.

Problems, constitution and advantageous effects other than the above will be clarified by descriptions of the following embodiments.

DESCRIPTION OF EMBODIMENTS

Hereinafter, embodiments according to the present invention will be described by way of the drawings and the like. The following descriptions are specific examples of the content of the present invention, and the present invention is not limited to these descriptions, and various changes and modifications by those skilled in the art may be made within the scope of the technical idea disclosed in the present description. Further in all the drawings to interpret the present invention, constituents having the same function are given the same reference sign, and repeated descriptions thereof may be omitted in some cases.

The adsorbent material according to the present invention comprises a polymer material having a plurality of functional groups ionizable in water (hereinafter, referred to also simply as a polymer material), an adsorption site capable of interacting with a target substance, and a carrier. The adsorbent material according to the present invention comprising these components leads to changes in the ionization rate of the polymer material in response to changes in the external environment, and the changes in the ionization rate make the target substance to be adsorbed or desorbed.

Figure 1:
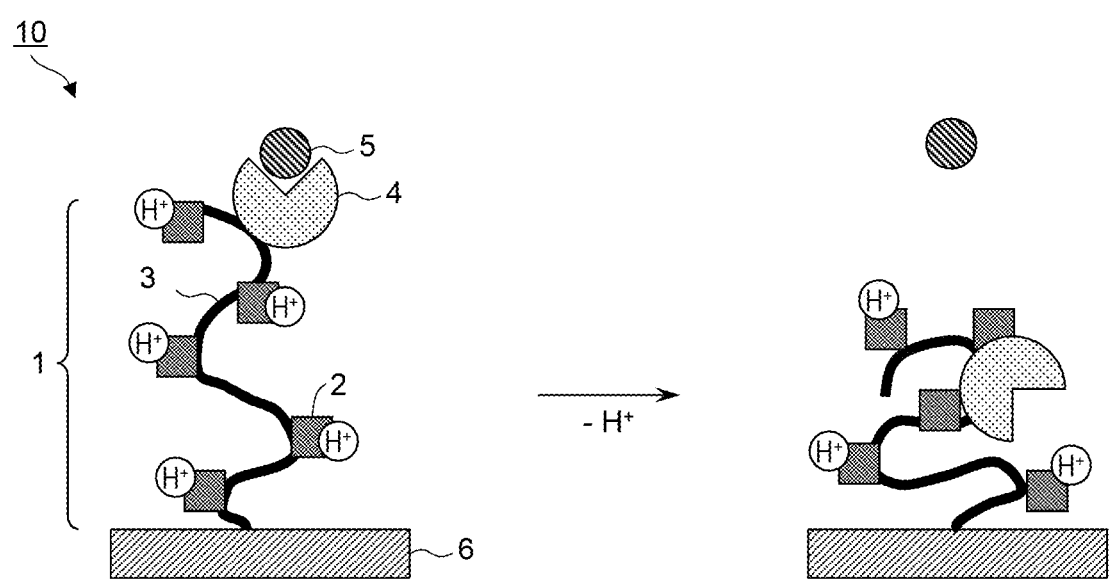
FIG. 1 is a schematic diagram of an adsorbent material in which a polymer material and an adsorption site are bound to each other.
Figure 2:
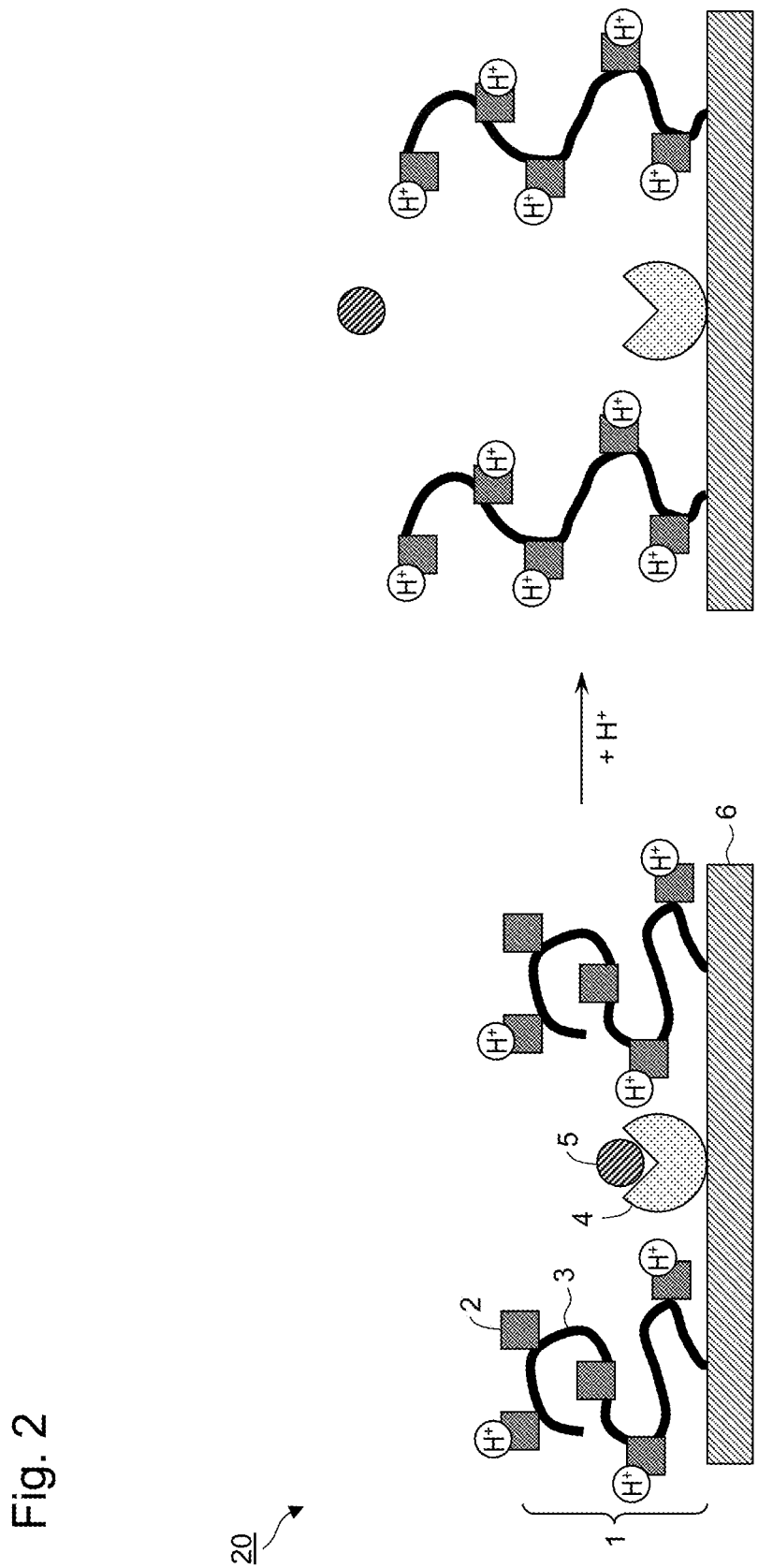
FIG. 2 is a schematic diagram of an adsorbent material in which a polymer material and an adsorption site are not bound to each other, but are immobilized separately at different positions on a carrier.

Schematic diagrams of adsorbent materials are shown in FIG. 1 and FIG. 2. As shown in FIG. 1 and FIG. 2, an adsorbent material 10 or an adsorbent material 20 comprises a polymer material 1 having a plurality of functional groups 2 ionizable in water on a polymer main chain 3, an adsorption site 4 capable of interacting with a target substance 5, and a carrier 6.

The polymer material and the adsorption site may be bound, or may be, without being mutually bound, separately immobilized on the carrier.

In one embodiment, a polymer material and an adsorption site are bound to each other. FIG. 1 shows a schematic diagram of an adsorbent material in which the polymer material and the adsorption site are bound to each other. As shown in FIG. 1, in the adsorbent material 10, the adsorption site 4 to adsorb the target substance 5 is bound to the polymer material 1 having a plurality of functional groups 2 ionizable in water. The polymer material 1 to which the adsorption site 4 has been bound is immobilized on the carrier 6.

In another embodiment, a polymer material and an adsorption site are not bound to each other but are immobilized separately at different positions on a carrier. FIG. 2 shows a schematic diagram of an adsorbent material in which the polymer material and the adsorption site are not bound to each other but are immobilized separately at different positions on the carrier. As shown in FIG. 2, in the adsorbent material 20, the adsorption site 4 to adsorb the target substance 5 is not bound to the polymer material 1 having a plurality of functional groups 2 ionizable in water, and the polymer material 1 and the adsorption site 4 are immobilized separately at different positions on the carrier 6.

The adsorbent material according to the present invention comprising the above-mentioned components, in particular, the polymer material having a plurality of functional groups ionizable in water, leads to changes in the ionization rate of the polymer material in response to changes in the external environment. Then, the change in the ionization rate of the polymer material results in a change in the peripheral environment of the adsorption site to interact with the target substance; as a result, the intensity of the interaction between the target substance and the adsorption site changes and the target substance is thereby adsorbed or desorbed.

In more detail, it is conceivable that when the ionization rate of the polymer material changes, the hydrophilicity and the conformation of the polymer material as a whole change. Although the polymer material, since having a plurality of functional groups ionizable in water, and exhibiting no lower limit critical solution temperature (LCST), is hydrophilic in either a high-ionization rate state or a low-ionization rate state, the polymer material is more hydrophilic in the high-ionization rate state and more hydrophobic in the low-ionization rate state. When the polymer material is in a high-ionization rate state, the functional groups ionizable in water are in a more ionized state, and the polymer main chain is likely to become in a relatively stretching state by charge repulsion among these ionized sites, whereas in a low-ionization rate state, since the charge repulsion is low, the polymer main chain is likely to become in a relatively shrinking state.

The presumption of the adsorption and desorption mechanism of the adsorbent material in which the polymer material and the adsorption site are bound to each other (see FIG. 1) will be described hereinafter. When the ionization rate of the polymer material is in a higher state, the functional groups ionizable in water is in a more ionized state, and the polymer main chain of the polymer material becomes in a relatively stretching state due to charge repulsion among ionized sites. At this time, in the case where the adsorption site is hydrophobic, since the interaction between the hydrophilic polymer material and the hydrophobic adsorption site is relatively weak, the target substance is adsorbed on the adsorption site (left figure of FIG. 1). Then, since when the ionization rate of the polymer material lowers in response to a change in the external environment, the hydrophobicity of the polymer material rises, in the case where the adsorption site is hydrophobic, the equilibrium moves in the direction in which the interaction between the polymer material and the adsorption site becomes strong, and resultantly, the adsorption of the target substance on the adsorption site weakens and the target substance is desorbed from the adsorption site (right figure of FIG. 1). In the state that the ionization rate of the polymer material lowers, the polymer main chain of the polymer material, since the charge repulsion is low, becomes in a relatively shrinking state.

The presumption of the adsorption and desorption mechanism of the adsorbent material (see FIG. 2) in which the polymer material and the adsorption site are not bound to each other but are immobilized separately at different positions on the carrier will be described hereinafter. When the ionization rate of the polymer material is in a higher state, the polymer main chain of the polymer material becomes in a relatively stretching state due to charge repulsion among ionized sites. At this time, since the excluded volume occupied on the carrier surface by the polymer material is larger, the target substance is desorbed from the adsorption site (right figure of FIG. 2). Then, when the ionization rate of the polymer material lowers in response to changes in the external environment, the amount of water of hydration in the periphery of the polymer material decreases and the excluded volume occupied on the carrier surface by the polymer material becomes small; thereby, the equilibrium moves in the direction in which it becomes easy for a solute to make access to the adsorption site present on the carrier surface, and resultantly, the target substance is adsorbed on the adsorption site (left figure of FIG. 2).

In the adsorbent material according to the present invention, even when the ionization rate of the polymer material lowers in response to changes in the external environment, since the polymer material does not become hydrophobic, the dispersibility in water is retained; and since the change in the solubility of the polymer material is not exploited, the hysteresis is low. Therefore, the adsorbent material according to the present invention is excellent in the dispersibility and the reversibility to conventional adsorbent materials exploiting the change in the solubility accompanying the temperature change, and is easy in handling when the adsorbent material is produced, transported and packed.

The change in an external environment is not especially limited as long as being able to change the ionization rate of the polymer material. Here, the ionization rate of the functional groups ionizable in water depends on the temperature dependency of the free energy ($\Delta G=\Delta H-T\Delta S$) relevant to the ionization, that is, on the degree of the entropy change ($\Delta S$) on the ionization, and since generally, $\Delta S \neq 0$, changes according to the temperature. That is, the change in an external environment is, for example, a temperature change. From the above expression, usually, the ionization rate lowers along with rising temperature, and rises along with falling temperature. Further since $\Delta H$ is affected also by the polarity of a solvent molecule, the degree of electrolytic dissociation, and the like, the change in an external environment includes, in addition to the temperature change, changes in salt concentration, permittivity, pH and the like of a solution in contact with the adsorbent material. For example, when the salt concentration is changed, the electrostatic shielding effect changes; when kinds of solvent and solute are changed, the permittivity changes; further when pH is changed, the equilibrium shift of ionization occurs, and these change the ionization rate. The change in an external environment is preferably changes in temperature, salt concentration, permittivity and pH of a solution in contact with the adsorbent material, and more preferably the temperature change. These changes in the external environment may be combined. The adsorbent material according to the present invention, since the target substance is adsorbed or desorbed in response to a change in the ionization rate of the polymer material in response to a change in the external environment, is an adsorbent material responsive to the change in the external environment; and for example, in the case where the change in an external environment is a temperature change, the adsorbent material is a temperature-responsive adsorbent material; and in the case where the change in an external environment is a change in salt concentration, permittivity or pH, the adsorbent material is a salt concentration-responsive, permittivity-responsive or pH-responsive adsorbent material, respectively.

The ionization rate of the polymer material can be determined, for example, by such a way that when an external environment is changed in the state that a buffer solution is passed through a column packed with the adsorbent material, a property (for example, pH) of the solution eluted from the column is monitored. For example, in the case where the change in an external environment is a temperature change (that is, the ionization rate of a polymer material is temperature-dependent), and the polymer material is one having, as the functional groups ionizable in water, functional groups such as amino groups, which are ionized by capturing protons from the neutral state, and in the case where the ionization rate lowers in response to a temperature change, the amount of the protons captured by the polymer material is reduced by changing the temperature of a column, and along therewith, the proton concentration in a buffer solution rises. Hence, by monitoring the pH of the solution eluted from the column, there is observed a region where the pH lowers by a magnitude corresponding to an amount of protons released from the polymer material. Conversely in the case where the ionization rate becomes high, since the polymer material deprives the buffer solution of protons, there is observed a region where the pH of the solution eluted from the column rises. It is clear that in the adsorbent material exhibiting these changes, the change in the ionization rate is temperature-dependent. Then, by quantitatively determining the number of molecules of the polymer material in the adsorbent material by titration, surface analysis, elemental analysis and the like, the width of the change in the ionization rate becomes enabled to be quantitatively determined.

The change in the ionization rate of the polymer material in response to the change in an external environment suffices if being a change in such a degree that the adsorption characteristic can be changed by changing the intensity of the interaction between the target substance and the adsorption site. This suffices, for example, if in the above measurement method of the ionization rate using a column packed with the adsorbent material, there is present a region where the pH of a solution eluted from the column changes by 0.7 or more in response to a change in an external environment.

The target substance is not especially limited as long as being a substance capable of being adsorbed on the adsorption site, but examples thereof include proteins, biomolecules, cells, viruses and nanoparticles. The target substance may be an antibody. Further from the viewpoint of making the best use of properties of the adsorbent material according to the present invention, target substances are suitable which are unstable in a severe pH condition.

The adsorption site can be selected according to the target substance to be adsorbed on the adsorption site. In the present invention, since adsorption and desorption of the target substance is controlled by exploiting the change in the ionization rate of the polymer material, it is preferable that the adsorption site be susceptible to changes in physical properties in response to the change in the ionization rate of the polymer material, and a hydrophobic adsorption site is preferable for the hydrophilic polymer material. Further it is preferable that the adsorption site have a size nearly equal to or smaller than the molecular size of the polymer material. Preferably, the adsorption site is hydrophobic and has a size nearly equal to or smaller than the molecular size of the polymer material. Then, the adsorption site may have functional groups ionizable in water, but in this case, in the adsorbent material in which the polymer material and the adsorption site are bound to each other, the functional groups ionizable in water which the adsorption site has cannot be the functional groups ionizable in water which the polymer material has. That is, the polymer material has, separately from the functional groups ionizable in water which the adsorption site has, functional groups ionizable in water.

The adsorption site is not especially limited, and examples thereof include peptides, proteins, sulfide group-containing (heterocyclic) aromatic compounds, vitamins, coloring matter, saccharides, sugar chain-bonding molecules, thiophilic ligands, boronic acid, antigens, antigen partial structures, substrates of enzymes, antibodies and antibody partial structures. The adsorption site suffices as long as having a moiety originated from these substances. Examples of the peptides and proteins include histidine tags, glutathiones, lectins and those having the RGD sequence. The peptides and proteins may be partial structures or mimetic molecules thereof. Examples of the partial structures or mimetic molecules of the peptides and proteins include protein A partial structures or mimetic molecules, protein G partial structures or mimetic molecules, and protein L partial structures or mimetic molecules; and examples of the mimetic molecules thereof include protein A mimetic molecules ApA, protein A mimetic molecules 22/8 and protein G mimetic molecules A2C7I1. Examples of the sulfide group-containing (heterocyclic) aromatic compounds include mercaptopyridine, mercaptoethylpyridine and (3-thia-5-pyridylpentyl) vinyl sulfone. Examples of the vitamines include biotin. Examples of the coloring matter include Rhodamine, Cibacron Blue and Mimetic Blue. Preferable adsorption sites are protein A partial structures or mimetic molecules, protein G partial structures or mimetic molecules, protein L partial structures or mimetic molecules, sugar chain-bonding molecules, thiophilic ligands, and antigens or antigen partial structures.

Examples of preferable combinations of the target substance and the adsorption site include combinations of an antibody and a protein A partial structure or mimetic molecule, or a sulfide group-containing (heterocyclic) aromatic compound, and combinations of a protein and a coloring matter or a vitamin.

The adsorption of the target substance on the adsorption site may be either a chemical binding or a physical binding, and may also be a multipoint binding. Reversible binding is formed, for example, by suitable interactions such as hydrogen bond, hydrophobic interaction, n-n interaction, dipole-dipole interaction, charge-dipole interaction, charge-charge interaction, charge transfer interaction, van der Waals binding and anchor effect, and by combinations thereof.

The functional groups ionizable in water which the polymer material has are not especially limited as long as being ionizable in water, but are preferably functional groups having a pKa of 17.7 or lower, where 17.7 is higher by 2 than 15.7, which is the pKa of water, and a pKa of −3.7 or higher, where −3.7 is lower by 2 than −1.7, which is the pKa of the oxonium ion in water, or functional groups to generate conjugate acids or conjugate bases having a pKa of 17.7 or lower, where 17.7 is higher by 2 than 15.7, which is the pKa of water, and a pKa of −3.7 or higher, where −3.7 is lower by 2 than −1.7, which is the pKa of the oxonium ion in water. That is, the functional groups ionizable in water preferably contain functional groups having a pKa of −3.7 or higher and 17.7 or lower, or functional groups whose conjugate acids or conjugate bases have a pKa of −3.7 or higher and 17.7 or lower. The functional groups ionizable in water suffice if at least a part of the functional groups or their conjugate acids or conjugate bases has the above-mentioned pKa. Here, there are some cases where an actual pKa when the functional group ionizable in water is present in the polymer material is different from a pKa when the functional group ionizable in water is singly present in water. This is because the presence in the polymer material of a plurality of functional groups ionizable in water causes an interaction among these groups in some cases.

A proper range of the pKa of the functional groups ionizable in water or their conjugate acids or conjugate bases differs depending on the pH when the adsorbent material is used. However, since by increasing the number of functional groups ionizable in water in the polymer material, the number of functional groups whose pKa is changed by the above-mentioned interaction increases and functional groups in a broad pKa range can be made to be contained in the polymer material, the pH range in which the adsorbent material according to the present invention can be used is sufficiently broad.

The functional groups ionizable in water are not especially limited, and there can be used, for example, an amino group (primary amino group, secondary amino group, tertiary amino group), an imino group, various types of nitrogen-containing aromatic groups (pyrrole group, imidazolyl group, pyridyl group, pyrimidyl group, oxazolyl group, thiazolyl group and triazolyl group), a guanidyl group, phenolic hydroxyl groups, a carboxyl group, a boronic acid group, a phosphoryl group, a phosphinyl group, a silicate group, and groups of derivatives thereof; preferable are an amino group, an imino group, nitrogen-containing aromatic groups, a guanidyl group, phenolic hydroxyl groups, a carboxyl group, a boronic acid group and a phosphoryl group; and especially preferable are an amino group and an imino group. The functional groups ionizable in water may be used singly or concurrently in a plurality of kinds thereof. When a plurality of kinds of the functional groups ionizable in water are used, since there is a possibility that the pKa largely changes due to the interaction among these and is out of a proper pKa range, it is preferable that these pKas be suitably set in the above-mentioned pKa range.

The polymer material having a plurality of functional groups ionizable in water is not especially limited as long as being one having a plurality of the above-mentioned ionizable functional groups. The polymer material may be a dendrimer. Examples of the polymer material include polylysine (α-polylysine, ε-polylysine), straight-chain polyethyleneimine, branched polyethyleneimine, polyvinylamine, chitosan, polyamideamine dendrimers, polypropyleneimine dendrimers, polylysine dendrimers, polyglutamic acid, polyaspartic acid, polyacrylic acid, polymethacrylic acid, carboxymethylcellulose, alginic acid, polyphosphoric acid, phlyphosphate esters, polysilicic acid, polysiloxane, derivatives thereof, and derivatives and copolymers having these as a partial structure. Preferable polymer materials are polylysine, dendrimers having a plurality of amino groups, dendrimers having a plurality of imino groups, polyethyleneimine, polyallylamine, and polymer materials having these as a partial structure. Here, the polylysine and polyallylamine have amino groups as functional groups ionizable in water; and the polyethyleneimine has imino groups as functional groups ionizable in water.

The polymer material having a plurality of functional groups ionizable in water exhibits no lower limit critical solution temperature (LCST). Hence, the polymer material according to the present invention is not one changing phases along with the temperature change. Further the polymer material is preferably hydrophilic. The adsorbent material according to the present invention, since the polymer material exhibiting no LCST, does not exploit changes in the solubility of the polymer material, and therefore is not one adsorbing or desorbing the target substance in response to the phase change. The adsorbent material according to the present invention is excellent in aspects of the dispersibility and the reversibility of response to conventional adsorbent materials using a temperature-responsive polymer exhibiting an LCST.

The carrier may be of either a porous shape or a nonporous shape. Examples of the shape of the carrier include shapes of plate form, bead form, fibrous form such as nonwoven fabrics and woven fabrics, film form, monolith form and hollow yarn form.

The carrier has a material containing, for example, a polysaccharide, a synthetic resin, an inorganic compound and a composite material thereof. The polysaccharide may be a crosslinked one. The carrier suffices if having these materials at least on the carrier surface. Examples of the polysaccharide or the crosslinked polysaccharide include agarose, crosslinked agarose, hydrophobized agarose and cellulose. Examples of the synthetic resin include polystyrene, polyalkyl methacrylate, polyglycidyl methacrylate, polyvinyl alcohol, polyvinylpyrrolidone, polyacrylamide, polysiloxane and polyfluoroethylene. The inorganic compound includes silica, metal oxides (for example, alumina, titania, zirconia and iron oxide), ferrite, hydroxyapatite and silicate. The carrier or its surface preferably has a polysaccharide, a crosslinked polysaccharide, polystyrene, silica or a metal oxide, and especially preferably has a polysaccharide or a crosslinked polysaccharide.

The carrier surface may be modified with a reactive group such as a carboxyl group, an amino group, a hydroxyl group, an epoxy group or an ester group. Further the carrier surface may be modified with a compound other than the adsorption site and the polymer material. There may be carried out on the carrier surface, for example, blocking to prevent non-specific adsorption of the target substance, surface modification to control the orientability of the adsorption site or the polymer material, modification to improve the dispersibility or adsorbability of the carrier, and the like.

The adsorbent material according to the present invention can be produced by chemically binding the polymer material, or the polymer material and the adsorption site on the carrier.

The chemical binding of the polymer material and the carrier may be formed, for example, by using the functional group ionizable in the polymer material. In this case, examples of combinations, for forming the chemical binding, of a functional group on the surface of the carrier and an ionizable functional group include an epoxy group and an amino group, an ester group (for example, an NHS ester of a carboxylic acid) and an amino group, and an amino group and a carboxyl group. The formation of the chemical binding can be carried out by contacting a solution of the polymer material with the carrier. In the case of forming the chemical binding by a condensation reaction (for example, in the case of using an amino group and a carboxyl group), the reaction is carried out preferably in the presence of a condensing agent (for example, DMT-MM).

In one embodiment, in the adsorbent material in which the polymer material and the adsorption site are bound to each other, the binding of the polymer material and the adsorption site may be formed either before or after the polymer material is immobilized on the carrier. That is, after the polymer material and the adsorption site are bound to each other, the polymer material to which the adsorption site has been bound may be immobilized on the carrier; or after the polymer material having no adsorption site is immobilized on the carrier, the immobilized polymer material and the adsorption site may be bound.

In another embodiment, the adsorbent material in which the polymer material and the adsorption site are not bound to each other but are immobilized separately at different positions on the carrier can be produced by separately immobilizing the polymer material and the adsorption site on the carrier. The immobilization of the polymer material on the carrier can be carried out as in the above. The immobilization of the adsorption site on the carrier can be carried out, for example, by causing the adsorption site and the carrier to be chemically bound. The order of the immobilization of the polymer material and the carrier is not especially limited, but it is preferable that the adsorption site be first immobilized on the carrier.

The present invention relates also to a method, for purifying a target substance, using the above-mentioned adsorbent material. The purification method of a target substance comprises a step of contacting a solution containing the target substance with the above-mentioned adsorption material, and then a step of applying a change in an above-mentioned external environment. The present invention can purify the target substance by causing the target substance to be adsorbed on the adsorbent material, or can also purify an objective substance by causing unnecessary substances as target substances to be adsorbed on the adsorbent material. In the latter case, for example, a cell can be purified by treating an unnecessary molecule on the cell membrane as the target substance, and a virus or a nanoparticle can be purified by treating an unnecessary molecule on the surface of the virus or the nanoparticle as the target substance.

In the step of contacting the solution containing the target substance with the adsorbent material, the target substance in the solution is adsorbed on the adsorbent material. The adsorption of the target substance on the adsorbent material can be achieved by suitably setting the ionization rate of the polymer material so that the target substance is adsorbed on the adsorption site. For example, in the adsorbent material in which the polymer material and the adsorption site are bound to each other, preferably, the target substance can be adsorbed on the adsorption site by more raising the ionization rate. Then, for example, in the adsorbent material in which the polymer material and the adsorption site are not bound to each other, but are immobilized separately at different positions on the carrier, preferably, the target substance can be adsorbed on the adsorption site by more lowering the ionization rate.

The temperature of the solution containing the target substance can be selected so that the target substance is adsorbed on the adsorbent material, but a temperature in the range where the target substance is stable is preferable, and a lower temperature in the range is more preferable. For example, in the adsorbent material in which the polymer material and the adsorption site are bound to each other, with respect to the temperature of the solution, a lower temperature in the range where the target substance is stable is preferable for adsorption, and is made to be, for example, 4° C. Then, for example, in the adsorbent material in which the polymer material and the adsorption site are not bound to each other, but are immobilized separately at different positions on the carrier, with respect to the temperature of the solution, a higher temperature in the range where the target substance is stable is preferable for adsorption, and is made to be, for example, 37° C.

It is preferable that the solution containing the target substance be made to be a buffer solution containing water as a solvent.

The pH when the solution containing the target substance is caused to contact with the adsorbent material can be selected depending on physical properties of the target substance, the adsorption site and the polymer material, but it is desirable to select a pH advantageous for adsorption of the target substance.

In the step of applying a change in an external environment, since the polymer material has a plurality of functional groups ionizable in water, by applying a change in an external environment, the ionization rate of the polymer material changes and the target substance is then desorbed from the adsorbent material. As the change in the external environment, the above-mentioned change can be used, and, for example, a change in temperature, salt concentration, permittivity (kinds of a solute and a solvent), pH or the like of the solution in contact with the adsorbent material is used.

In one embodiment, the purification method of the target substance is carried out by using a column packed with the adsorbent material. In conventional temperature-responsive adsorbent materials exploiting changes in the solubility, in response to temperature changes, the hydrophobicity increases and the dispersibility decreases, and the affinity for water largely changes, so there are such risks that flow paths in the column change and cracks and gaps between the adsorbent material and the wall surface are generated; however, in the adsorbent material according to the present invention, since the change in the solubility along with the temperature change is not exploited for adsorption or desorption of the target substance, such risks are low.

It is preferable that the purification method using a column packed with the adsorbent material according to the present invention, from the viewpoint of making the best use of its characteristics, be applied to objects in which decomposition and aggregate formation are generated at a low pH. Further since an eluted target substance is obtained in the state of being dissolved in a buffer solution in a pH region near neutral, a neutralization step is not needed and the eluted target substance can be applied to the next purification process.

In another embodiment, the purification method of the target substance is carried out by using the adsorbent material in the state of a suspension. In conventional temperature-responsive adsorbent materials exploiting changes in the solubility, in response to temperature changes, the hydrophobicity increases and the dispersibility lowers, and there then arise high risks of aggregation, adhesion on the wall surface, localization at interfaces and the like of the adsorbent material in the suspension state; however, the adsorbent material according to the present invention, since not exploiting the change in the solubility along with the temperature change for adsorption or desorption of the target substance, almost does not pose such risks.

Hereinafter, the present invention will be described specifically by way of Examples, but the technical scope of the present invention is not any more limited thereto.

EXAMPLES

Example 1

As the polymer material having a plurality of functional groups ionizable in water, a polyamine was used. Specifically, a human IgG antibody was treated as the target substance; an ε-polylysine (EPL) was used as the polymer material; and (4-hydroxyphenylethylamino)(phenylamino)triazine (ApA) was treated as the adsorption site. Here, ApA was a protein A mimetic molecule having an antibody adsorption capability.

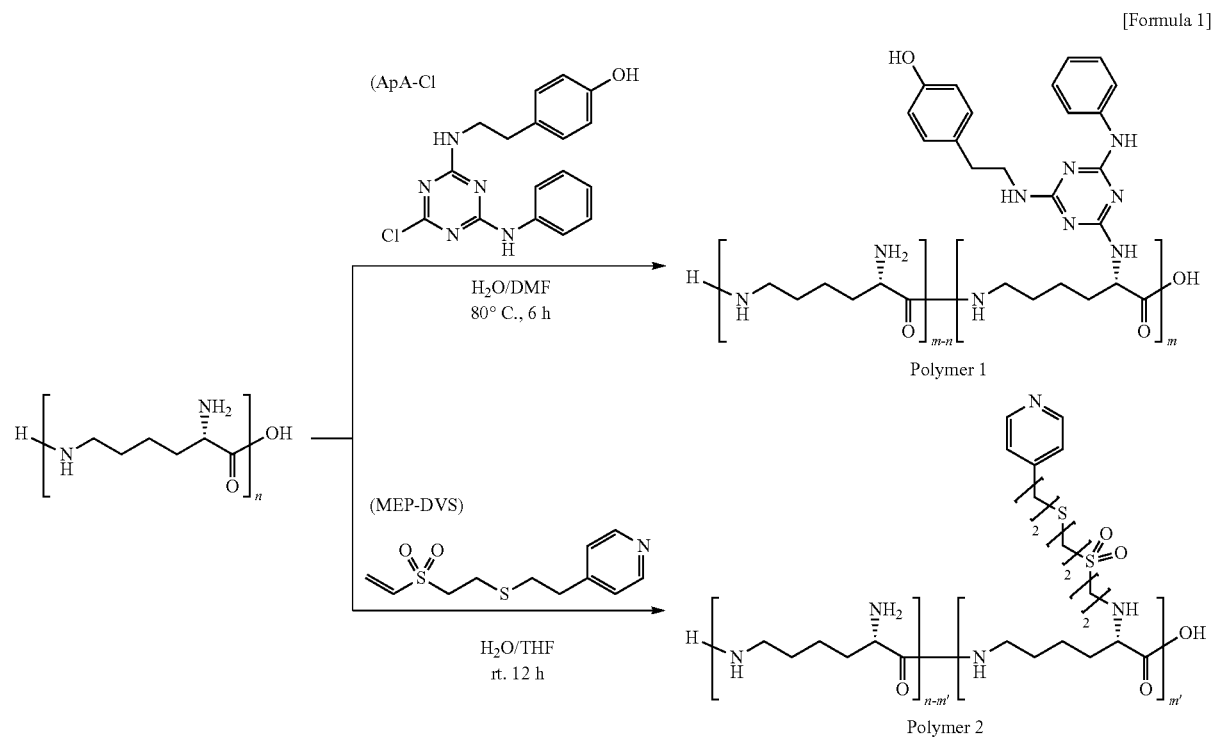

[Formula 1]

Chloro(4-hydroxyphenylethylamino)(phenylamino)triazine (ApA-C) (0.2 equivalent) and triethylamine (0.02 equivalent) were added to a water/DMF solution of EPL, and heated at 80° C. for 6 hours to thereby introduce ApA to EPL. Hydrochloric acid was added to an obtained reaction solution to render the solution acidic; the resultant solution was dialyzed with water; a produced precipitate was filtered off and thereafter lyophilized to thereby obtain Polymer 1 as a solid.

A 0.1-wt % solution of the obtained Polymer 1 was prepared, and added to a crosslinked agarose carrier having NHS ester groups on its surface; and an obtained suspension was shaken at room temperature overnight to thereby obtain an adsorbent material of Example 1 in which Polymer 1 was immobilized on the carrier.

Example 2

A human IgG antibody was treated as the target substance; EPL was used as the polymer material; and a (3-thia-5-pyridylpentyl)sulfonylethyl moiety derived from (3-thia-5-pyridylpentyl) vinyl sulfone (MEP-DVS) was treated as the adsorption site.

Divinyl sulfone and a 2-pyridylethanethiol hydrochloric acid salt were allowed to react in the presence of a base to thereby prepare (3-thia-5-pyridylpentyl) vinyl sulfone (MEP-DVS). A THF solution of MEP-DVS (0.7 equivalent) was added to a water/THF solution of EPL, and stirred at room temperature for 12 hours to thereby introduce a (3-thia-5-pyridylpentyl)sulfonylethyl moiety derived from MEP-DVS to EPL. Hydrochloric acid was added to an obtained reaction solution to render the solution acidic; the resultant solution was dialyzed with water; a produced precipitate was filtered off and thereafter lyophilized to thereby obtain Polymer 2 as a solid.

An adsorbent material of Example 2 in which Polymer 2 was immobilized on the carrier was obtained as in Example 1.

Examples 3 to 6

Adsorbent materials of Examples 3 to 6 were obtained by using combinations of various types of polymer materials and adsorption sites. Specifically, a corresponding polymer material and a corresponding compound (1 to 20 equivalents) for forming a corresponding adsorption site, shown in Table 1, were mixed and allowed to react under a predetermined condition to synthesize Polymers 3 to 6; and the obtained Polymers were immobilized on the carriers as in Example 1 to thereby obtain adsorbent materials of Examples 3 to 6, respectively.

Example 7

EPL was used as the polymer material and ApA was treated as the adsorption site. ApA was immobilized on a crosslinked agarose carrier having NHS ester groups on its surface as in the case of the immobilization of Polymer 1 on the carrier in Example 1; and thereafter, EPL was immobilized on the carrier to thereby obtain an adsorbent material of Example 7 in which ApA and EPL were immobilized separately on the carrier.

Comparative Example 1

Divinyl sulfone (DVS) was caused to act on a crosslinked agarose carrier in the presence of NaOH, and thereafter, a 2-pyridylethanethiol (MEP) hydrochloric acid salt was caused to act thereon to thereby obtain an adsorbent material of Comparative Example 1 in which a (3-thia-5-pyridylpentyl)sulfonylethyl moiety derived from MEP-DVS was introduced on the carrier.

Comparative Example 2

A DMF solution of a chlorotriazine derivative being a raw material of a protein A mimetic molecule 22/8 was caused to act on a crosslinked agarose carrier having amino groups on its surface to thereby obtain an adsorbent material of Comparative Example 2 in which the protein A mimetic molecule 22/8 was introduced on the carrier.

Comparative Example 3

A human IgG antibody was immobilized on a crosslinked agarose carrier to obtain an adsorbent material of Comparative Example 3 in which the human IgG antibody was introduced on the carrier.

Comparative Example 4

A 0.1 wt % solution of a polyamideamine dendrimer was added to a crosslinked agarose carrier having NHS ester groups on its surface; and an obtained suspension was shaken at room temperature overnight to thereby obtain an adsorbent material of Comparative Example 4 in which the polyamideamine dendrimer was immobilized on the carrier.

Comparative Example 5

A crosslinked agarose carrier was used as an adsorbent material of Comparative Example 5.

For the adsorbent materials of Examples 1 to 7 and Comparative Examples 1 to 5, polymer materials, adsorption sites and preferable target substances are shown in Table 1. Here, with respect to the adsorption sites, there are described the adsorption sites introduced or raw material compounds used for introduction of the adsorption sites.

TABLE 1

|  | Polymer material | Adsorption site | Target substance |
| --- | --- | --- | --- |
| Example 1 | ε-polylysine | ApA | antibody |
| Example 2 | ε-polylysine | MEP-DVS | antibody |
| Example 3 | ε-polylysine | Rhodamine B | trypsin |
| Example 4 | polyamideamine dendrimer | ApA | antibody |
| Example 5 | branched polyethyleneimine | Cibacron Blue | albumin |
| Example 6 | polyglutamic acid | biotin | streptoavidin |
| Example 7 | ε-polylysine | ApA (immobilized on carrier) | antibody |
| Comparative Example 1 | — | MEP-DVS | antibody |
| Comparative Example 2 | — | 22/8 | antibody |
| Comparative Example 3 | — | human IgG | protein A |
| Comparative Example 4 | polyamideamine dendrimer | — | — |
| Comparative Example 5 | — | — | — |

Test Example 1

For the adsorbent materials of Examples 1 to 7 and Comparative Examples 1 to 5, changes in the ionization rate along with temperature changes were measured.

Figure 3:
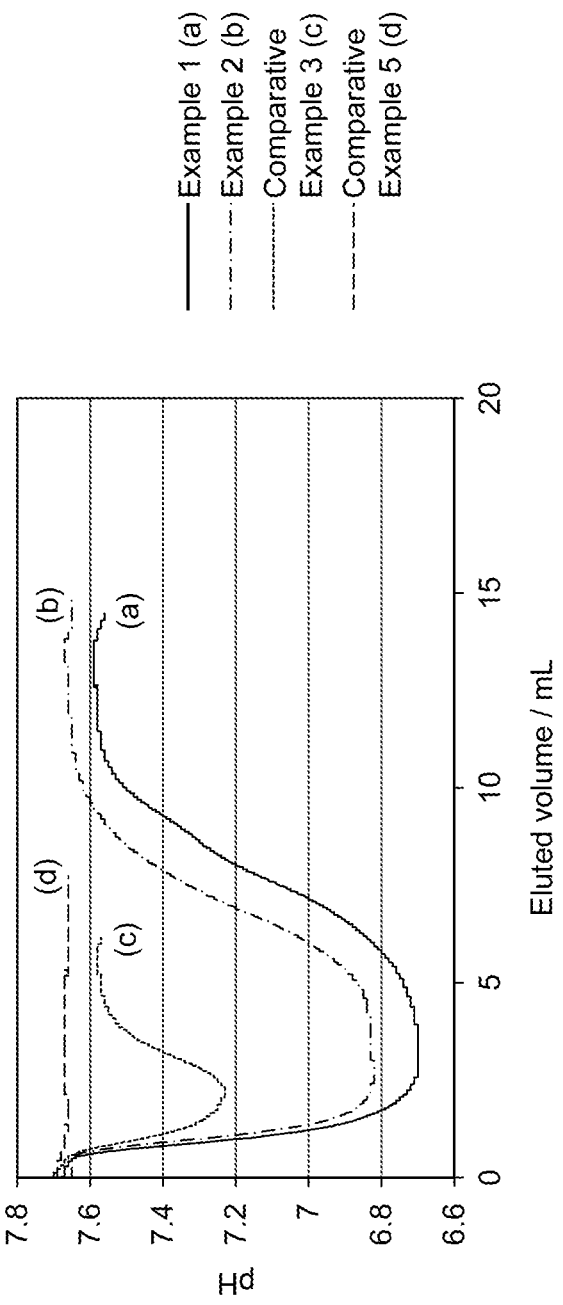
FIG. 3 is a diagram showing measurement results of changes in ionization rates of adsorbent materials when being heated from 4° C. to 37° C., in Examples.

The each adsorbent material was packed in a column (inner diameter: 5 mm, length: 50 mm), and set in a 4° C. thermostatic chamber; a PBS buffer solution (5 mM) was passed at a flow volume of 0.5 mL/min through the column to stabilize the column at 4° C. Thereafter, the column was set in a 37° C. thermostatic chamber in the state that the flow volume (0.5 mL/min) was kept; and the pH of a solution eluted from the column was monitored. The results for the adsorbent materials of Examples 1 and 2 and Compara- Examples 3 and 5 are shown in FIG. 3 as representative examples. FIG. 3 shows the measurement results of changes in the ionization rates of the adsorbent materials of Examples 1 and 2 and Comparative Examples 3 and 5 when the adsorbent materials were heated from 4° C. to 37° C.

Figure 4:
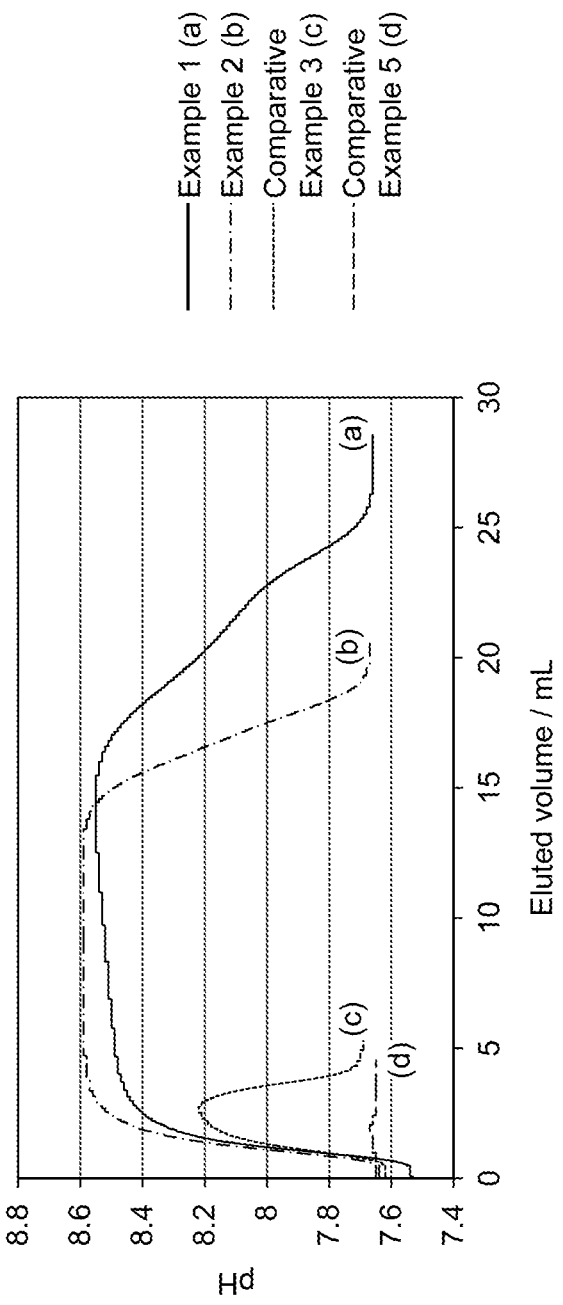
FIG. 4 is a diagram showing measurement results of changes in ionization rates of adsorbent materials when being cooled from 37° C. to 4° C., in Examples.
Figure 5:
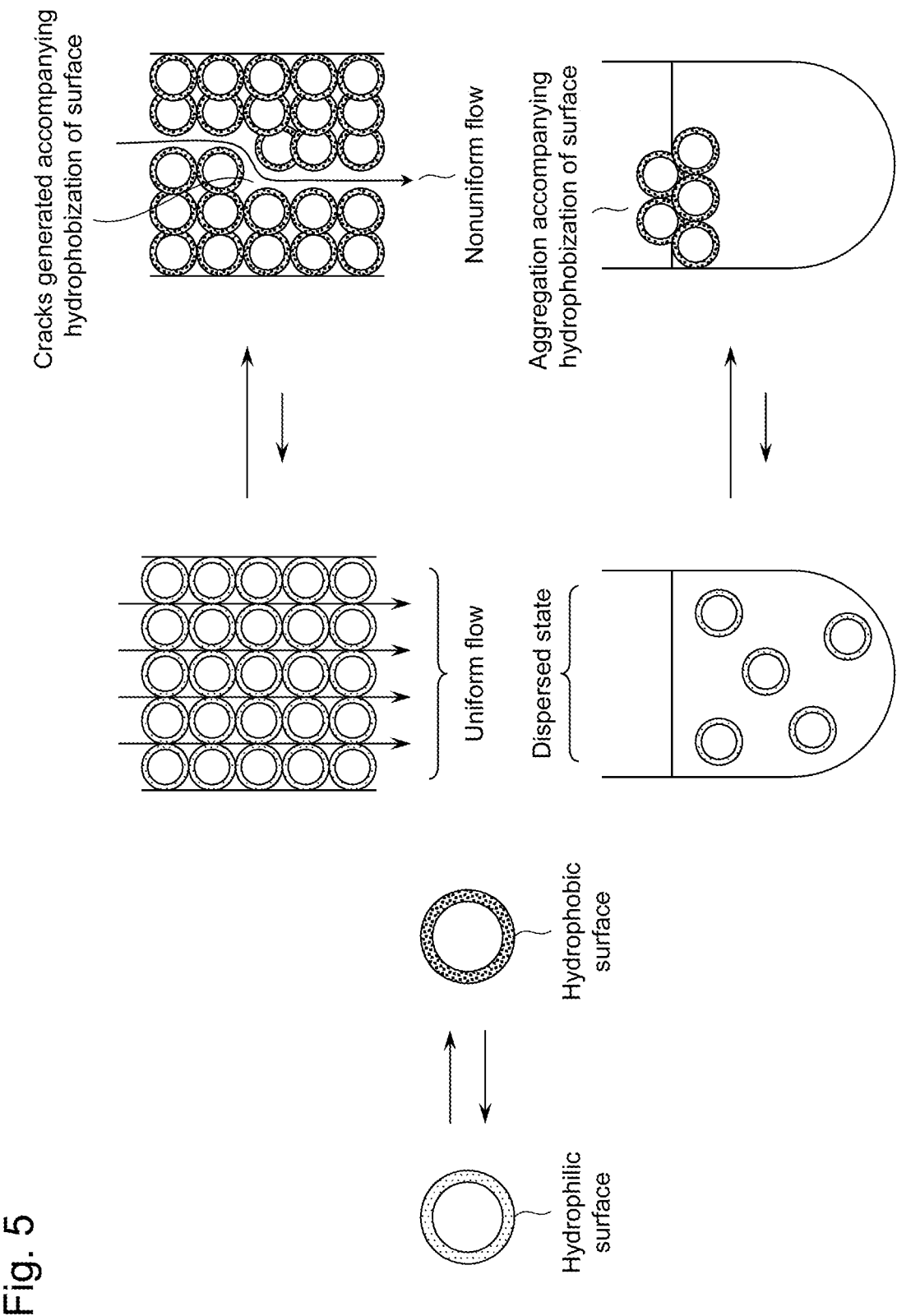
FIG. 5 is a schematic diagram illustrating the problem when a conventional adsorbent material exploiting changes in the solubility of a polymer is used.

Then, after the column was stabilized at 37° C., the column was again set in the 4° C. thermostatic chamber in the state that the above flow volume (0.5 mL/min) was kept; and the pH of a solution eluted from the column was monitored. The results for the adsorbent materials of Examples 1 and 2 and Comparative Examples 3 and 5 are shown in FIG. 4 as representative examples. FIG. 4 shows the measurement results of changes in the ionization rates of the adsorbent materials of Examples 1 and 2 and Comparative Examples 3 and 5 when the adsorbent materials were cooled from 37° C. to 4° C.

From FIG. 3 and FIG. 4, in the adsorbent material of Comparative Example 3, the pH change of the solution eluted from the column along with the temperature changes was small; and in the adsorbent material of Comparative Example 5, no pH change of the solution eluted from the column was observed. By contrast, in the adsorbent materials of Examples 1 and 2, the pH changes of the solutions eluted from the columns along with the temperature changes were large as compared with the adsorbent materials of Comparative Examples 3 and 5, revealing that the ionization rates largely changed along with the temperature changes. Here, though not shown in figure, the adsorbent materials of Examples 3 to 7 also had large pH changes of the solutions eluted from the columns along with the temperature changes, similarly to the adsorbent materials of Examples 1 and 2, as compared with the adsorbent materials of Comparative Examples, revealing that the ionization rates largely changed along with the temperature changes. Hence, it is revealed that by using the polymer material having a plurality of functional groups ionizable in water, the ionization rates of the polymer materials largely changed along with the temperature changes.

Test Example 2

The changes in the adsorption characteristics for the target substances along with the temperature changes of the adsorbent materials of Examples 1 to 7 and the adsorbent materials of Comparative Examples 1 to 5 were measured in columns.

10 mL of a PBS buffer solution (5 mM or 30 mM phosphoric acid, 37.5 mM sodium chloride) of pH 7.4 containing 1% by weight of a predetermined target substance was passed at 4° C. or 37° C. through a column; the target substance concentration in a solution eluted from the column was monitored and the adsorption capacity of the adsorbent material was calculated from an amount corresponding to a reduced concentration of the target substance in the solution. The results of Examples 1, 2, 4, 6 and 7 and Comparative Examples 2, 3 and 5 are shown in Table 2 as representative examples.

TABLE 2

| | 4° C. | 37° C. | Target substance | Desorption rate |
|---|---|---|---|---|
| Example 1 | 17 mg | 8 mg (5 mM) | human IgG | ~53% |
| | | 3 mg (30 mM) | | ~82% |
| Example 2 | 14 mg | 5 mg (5 mM) | human IgG | ~64% |
| | | 1 mg (30 mM) | | ~93% |

TABLE 2-continued

| | 4° C. | 37° C. | Target substance | Desorption rate |
|---|---|---|---|---|
| Example 4 | 10 mg | 3 mg (30 mM) | human IgG | ~70% |
| Example 6 | 5 mg | 1 mg | streptoavidin-peroxidase complex | ~80% |
| Example 7 | 4 mg | 9 mg | human IgG | ~56% |
| Comparative Example 2 | 4 mg | 4 mg | rabbit IgG | ~0% |
| Comparative Example 3 | 2 mg | 2 mg | protein A | ~0% |
| Comparative Example 5 | <0.1 mg | <0.1 mg | human IgG | N/A |

From Table 2, in Test Example 1, the adsorbent materials of Examples 1, 2, 4, 6 and 7, which had large changes in the ionization rates of the polymer materials along with the temperature changes, as compared with the adsorbent materials of Comparative Examples 2, 3 and 5, had high desorption rates, exhibited excellent adsorption characteristics and also exhibited temperature dependencies of the adsorption characteristics. In the adsorbent materials of Examples 1, 2, 4 and 6, in which the polymer material and the adsorption site were bound, the target substance was desorbed in the temperature-rising time, whereas in the adsorbent material of Example 7, in which the polymer material and the adsorption site were immobilized separately on the carrier, the target substance was desorbed in the temperature-falling time. By contrast, in the adsorbent materials of Comparative Examples 1 to 4, although changes in the ionization rates of the polymer materials along with the temperature changes were small in Test Example 1, the desorption rates were low and almost no temperature dependencies of the adsorption characteristics were observed. Then, the adsorbent materials of Examples 3 and 5 similarly exhibited adsorption characteristics superior to the adsorbent materials of Comparative Examples, and also exhibited temperature dependencies of the adsorption characteristics.

Test Example 3

Changes in the adsorption characteristics for the target substances along with the temperature changes of the adsorbent materials of Examples 1 to 7 and the adsorbent materials of Comparative Examples 1 to 5 were measured in a bead dispersion system using the adsorbent materials in a suspension state.

To each of the adsorbent material, a volume twice the volume of the beads of a PBS buffer solution (5 mM or 30 mM phosphoric acid, 37.5 mM sodium chloride) of pH 7.4 containing 1% by weight of a predetermined target substance was added at 4° C. or 37° C., and shaken for 3 hours; thereafter, a supernatant solution was analyzed by GPC and an amount corresponding to a reduced concentration of the target substance was quantitatively determined to thereby calculate the adsorption capacity of the adsorbent material. The results of Examples 1 and 2 and Comparative Examples 2, 3 and 5 are shown in Table 3 as representative examples.

TABLE 3

| | 4° C. | 37° C. | Target substance | Desorption rate |
|---|---|---|---|---|
| Example 1 | 14 mg | 7 mg (5 mM) | human IgG | ~50% |
| | | 2 mg (30 mM) | | ~86% |

TABLE 3-continued

| | 4° C. | 37° C. | Target substance | Desorption rate |
|---|---|---|---|---|
| Example 2 | 15 mg | 5 mg (30 mM) | human IgG | ~67% |
| Comparative Example 2 | 3 mg | 3 mg | rabbit IgG | ~0% |
| Comparative Example 3 | 2 mg | 2 mg | protein A | ~0% |
| Comparative Example 5 | <0.1 mg | <0.1 mg | human IgG | N/A |

From Table 3, in Test Example 1, the adsorbent materials of Examples 1 and 2, which had large changes in the ionization rates of the polymer materials along with the temperature changes, as compared with the adsorbent materials of Comparative Examples 2, 3 and 5, had high desorption rates, exhibited excellent adsorption characteristics and also exhibited temperature dependencies of the adsorption characteristics. By contrast, in the adsorbent materials of Comparative Examples 1 to 4, although changes in the ionization rates of the polymer materials along with the temperature changes were small in Test Example 1, the desorption rates were low and almost no temperature dependencies of the adsorption characteristics were observed. Then, the adsorbent materials of Examples 3 to 7 similarly exhibited adsorption characteristics superior to the adsorbent materials of Comparative Examples, and also exhibited temperature dependencies of the adsorption characteristics.

REFERENCE SIGNS LIST

10 Adsorbent material
20 Adsorbent material
1 Polymer material
2 Functional group ionizable in water
3 Polymer main chain
4 Adsorption site
5 Target substance
6 Carrier All publications, patents and patent applications cited in the present description are to be incorporated as they are as citations in the present description.

The invention claimed is:

1. An adsorbent material, comprising:
    a polymer material having a plurality of functional groups ionizable in water and exhibiting no lower limit critical solution temperature;
    an adsorption site capable of interacting with a target substance; and
    a carrier,
    wherein the polymer material is a polylysine, a dendrimer having a plurality of amino groups, a dendrimer having a plurality of imino groups, a polyethyleneimine, a polyallylamine, a polyglutamic acid, or a polymer material having these as a partial structure;
    wherein the adsorption site is at least one selected from protein A partial structures or mimetic molecules, protein G partial structures or mimetic molecules, protein L partial structures or mimetic molecules, sugar chain-bonding molecules, thiophilic ligands, and antigens or antigen partial structures; and
    wherein the polymer material and the adsorption site are directly bound to each other, or the polymer material and the adsorption site are not bound to each other, but are immobilized at different positions on the carrier.

2. The adsorbent material according to claim 1, wherein an ionization rate of the polymer material changes in response to a change in an external environment.

3. The adsorbent material according to claim 2, wherein the change in an external environment is a change in temperature, salt concentration, permittivity or pH of a solution in contact with the adsorbent material.

4. The adsorbent material according to claim 1, wherein the target substance is a protein, a biomolecule, a cell, a virus or a nanoparticle.

5. The adsorbent material according to claim 4, wherein the target substance is an antibody.

6. The adsorbent material according to claim 1, wherein the carrier or a surface thereof has a polysaccharide, a crosslinked polysaccharide, polystyrene, silica or a metal oxide.

7. The adsorbent material according to claim 6, wherein the carrier or a surface thereof has a polysaccharide or a crosslinked polysaccharide.

8. A method for purifying a target substance, comprising:
    contacting a solution comprising the target substance with an adsorbent material comprising,
        a polymer material having a plurality of functional groups ionizable in water and exhibiting no lower limit critical solution temperature;
        an adsorption site capable of interacting with the target substance; and
        a carrier,
        wherein the polymer material is a polylysine, a dendrimer having a plurality of amino groups, a dendrimer having a plurality of imino groups, a polyethyleneimine, a polyallylamine, a polyglutamic acid, or a polymer material having these as a partial structure;
        wherein the adsorption site is at least one selected from protein A partial structures or mimetic molecules, protein G partial structures or mimetic molecules, protein L partial structures or mimetic molecules, sugar chain-bonding molecules, thiophilic ligands, and antigens or antigen partial structures; and
        wherein the polymer material and the adsorption site are directly bound to each other, or the polymer material and the adsorption site are not bound to each other, but are immobilized at different positions on the carrier; and
    applying a change in an external environment wherein
        an ionization rate of the polymer material changes in response to the change in the external environment, and
        the change in the external environment is a change in temperature, salt concentration, permittivity or pH of a solution in contact with the adsorbent material.

9. The purification method according to claim 8, wherein a column is packed with the adsorbent material.

10. The purification method according to claim 8, wherein the adsorbent material is used in a state of a suspension.

* * * * *